(12) United States Patent
Wang et al.

(10) Patent No.: US 7,692,015 B2
(45) Date of Patent: Apr. 6, 2010

(54) ECONOMICAL PROCESS FOR PREPARING (S, S)-2, 8-DIAZABICYCLO[4.3.0]NONANE AND ITS ENANTIOMER

(76) Inventors: Zheqing Wang, 15 Blake Ct., East Haven, CT (US) 06512; Shushan Feng, 33 Zhenyun Road, Houzui, Development Zone, Lianyungang City (CN) 222069; Yongzhi Cheng, 33 Zhenyun Road, Houzui, Development Zone, Lianyungang City (CN) 222069

( * ) Notice: Subject to any disclaimer, the term of this patent is extended or adjusted under 35 U.S.C. 154(b) by 114 days.

(21) Appl. No.: 12/004,822

(22) Filed: Dec. 21, 2007

(65) Prior Publication Data

US 2008/0221329 A1    Sep. 11, 2008

Related U.S. Application Data

(60) Provisional application No. 60/878,760, filed on Jan. 5, 2007.

(51) Int. Cl.
*C07D 471/04*    (2006.01)
(52) U.S. Cl. ..................................... 546/113
(58) Field of Classification Search .................. 546/113
See application file for complete search history.

(56) References Cited

U.S. PATENT DOCUMENTS 3,709,894 A    1/1973  Klemm et al.
5,059,597 A    10/1991 Peterson et al.
5,436,334 A    7/1995  Schenke et al.
5,480,879 A    1/1996  Peterson et al.
5,770,597 A *  6/1998  Kim et al. ................ 514/230.2
6,153,414 A    11/2000 Drisbach
6,235,908 B1   5/2001  Fey

FOREIGN PATENT DOCUMENTS

EP    0350733 B1   6/1989
EP    0550903 A1   12/1992

OTHER PUBLICATIONS

Weisblat, et al., "The Cleavage of Sulfonamides," J. Am. Chem. Soc., (1953) 75: 3630-3632.
Klemm, et al., "Chemistry of Thienopyridines. X. Syntheses of Thieno[3,4-b]—and Thieno [3,4-c] pyridines (I)," J. Heterocyclic Chem. (1970), 7: 463-464.
Armarego, et al., "Synthesis and Stability of 2-Methyl-2,4-diaza- and 2-Methyl-2,5-diaza-indene (2-Methyl-pyrrolo[3,4-b]pyridine and -pyrrolo[3,4-c]pyridine)," J. Chem. Soc. Perkin Trans. (1972), 1:2485-2490.
Greene, et al., "Protective Groups in Organic Synthesis," John Wiley & Sons (1991), 377-386.

* cited by examiner

*Primary Examiner*—Patricia L Morris
(74) *Attorney, Agent, or Firm*—Cantor Colburn LLP

(57) ABSTRACT

The present invention relates to a novel and economical process for preparing (S,S)-2,8-diazabicyclo[4.3.0]nonane, a valuable intermediate used for constructing quinolone and naphthyridine derivatives having antibacterial effectiveness, e.g. moxifloxacin and its enantiomer.

12 Claims, No Drawings

ECONOMICAL PROCESS FOR PREPARING (S, S)-2, 8-DIAZABICYCLO[4.3.0]NONANE AND ITS ENANTIOMER

This application claims the benefit of U.S. Provisional Application No. 60/878,760 filed on Jan. 5, 2007.

BACKGROUND OF THE INVENTION

The present invention relates to a novel and economical process for preparing (S,S)-2,8-diazabicyclo[4.3.0]nonane of formula I-a, a valuable intermediate used for constructing quinolone and naphthyridine derivatives having antibacterial effectiveness, e.g. moxifloxacin, and its enantiomer I-b.

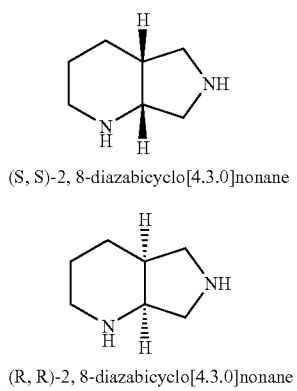

(S, S)-2, 8-diazabicyclo[4.3.0]nonane    Formula I-a (R, R)-2, 8-diazabicyclo[4.3.0]nonane    Formula I-b The preparation of (S,S)-2,8-diazabicyclo[4.3.0]nonane of formula I-a is showing in scheme 1.

The intermediate, racemic cis-(S,S/R,R)-8-benzyl-2,8-diazabicyclo[4.3.0]nonane of formula IV described in EP 0350733B1 is prepared via the coupling of pyridine-2,3-dicarboxylic acid with benzylamine to form 6-benzyl-pyrrolo[3,4-b]pyridine-5,7-dione of formula II, followed by de-aromatization via catalytic hydrogenation to generate formula III and LAH reduction to remove di-carbonyl groups.

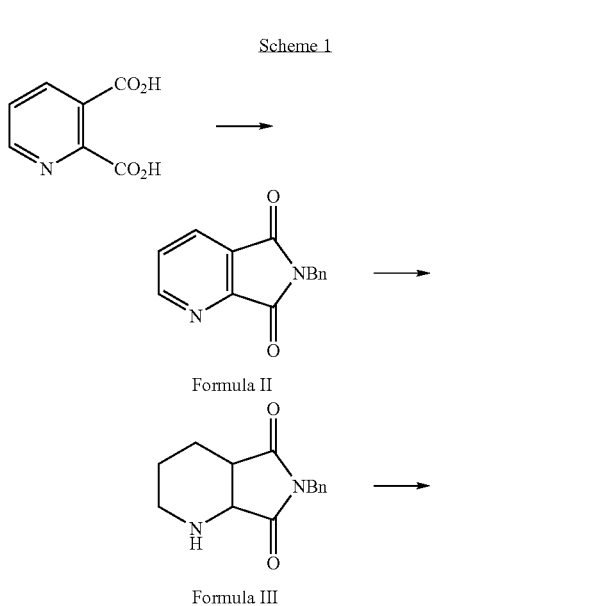

Scheme 1

Formula II

Formula III

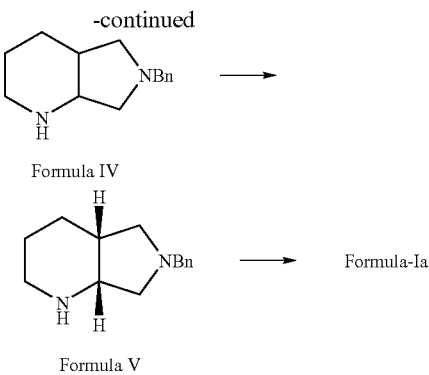

Formula IV

Formula V → Formula-Ia

To obtain the desired enantiomer the racemic IV needs to be separated. Two methods for the resolution are disclosed by EP 0550903 and U.S. Pat. No. 5,480,879.

One method is using nature L-(+)-tartaric acid as resolution agent and DMF, an expensive solvent, as resolution solvent. The desired enantiomer of (S,S)-benzylpyrrolopiperidine L-(+)-tartrate of formula V is crystallized out subsequently from racemic cis-(S,S/R,R)-8-benzyl-2,8-diazabicyclo[4.3.0]nonane tartrate solution since undesired R,R-enantiomer salt is required prior removal.

Alternatively, the S,S-enantiomer salt can precipitate first if D-(−)-tartaric acid is used. But, the application of the second method to the manufacture can be ruled out owing to the high cost of the unnatural D-(−)-tartaric acid.

By using same resolution reagent, L-(+)-tartaric acid, U.S. Pat. No. 6,235,908 makes improvement on the resolution method for the same intermediate of formula IV, wherein expensive DMF is replaced by 1-butanol or an alcohol/water solvent mixture.

The desired S,S-enantiomer of formula V from separation is then subjected to remove benzyl group by catalytic hydrogenation to give the title compound (S,S)-2,8-diazabicyclo[4.3.0]nonane of formula I-a.

U.S. Pat. No. 5,770,597 discloses a different approach to prepare racemic mixture of cis-(S,S/R,R)-2,8-diazabicyclo[4.3.0]nonane of formula IX as showing in scheme 2.

Scheme 2

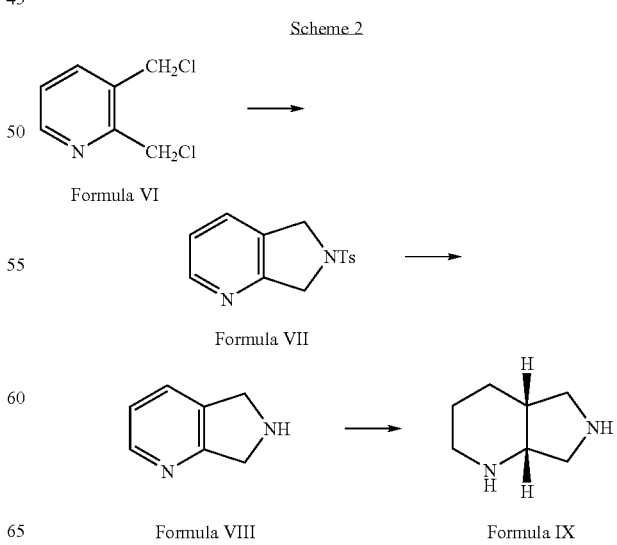

Formula VI

Formula VII

Formula VIII    Formula IX

The first step, alkylation on toluene-4-sulfonamide with 2,3-dichloromethylpyridine of formula VI is performed following the method released by W. L. F. Armarego et al in *J. Chem. Soc. Perkin Trans.* 1, 2485 (1972) to form 2,3-dihydro-2-p-toluene sulfonyl-1H-pyrrolo[2,3,c]pyridine of formula VII, which is treated with HBr/HAc to remove toluene-sulfonyl group instructed by the method of Weisblat et al published in *J. Am. Chem. Soc.* 75, 3630 (1953) to form the compound VIII. And finally, the catalytic hydrogenation reduces pyridine ring of formula VIII to give cis-(S,S/R,R)-2,8-diazabicyclo[4.3.0]nonane of formula IX as a racemic mixture.

The disadvantages of the method is that the first reaction carrying on in slurry formed by DMF and NaH. NaH is a reagent of difficult to be handling and working up. Hydrogen gas is generated during whole reaction period. Furthermore, NaH and DMF mixture system has been reported to cause explosive accidents many times. Therefore, there is less practical value for the manufacture. Obviously, the route is permitted only for preparing the racemate.

SUMMARY OF THE INVENTION

After intensive investigations the inventors succeed in developing a novel and economical process for preparing (S,S)-2,8-diazabicyclo[4.3.0]nonane of formula I-a as well as its enantionmer (R,R)-2,8-diazabicyclo[4.3.0]nonane of Formula I-b.

The present process showing in Scheme 3 is endowed with the advantages of consisting of only four steps including the resolution, very high efficient resolutions and safe reaction conditions.

Scheme 3

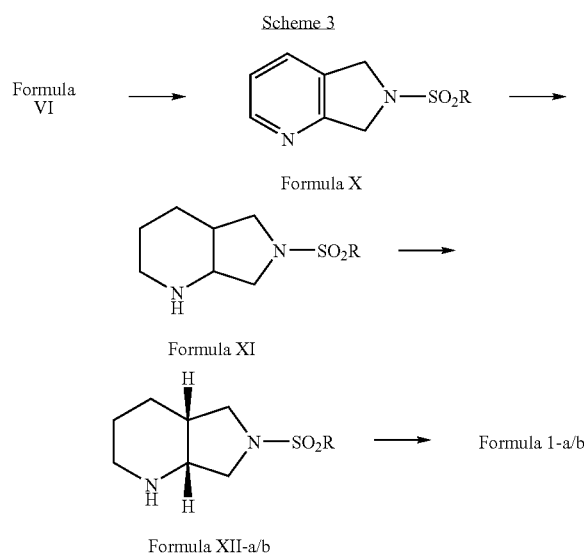

The process for the preparing (S,S)-2,8-diazabicyclo[4.3.0]nonane and its enantionmer comprising the steps of (1). condensation 2,3-halomethylpyridine of formula VI with appropriate substituted sulfonamide to form 6-substituted sulfonyl-6,7-dihydro-5H-pyrrolo[3,4-b]pyridine of Formula X;

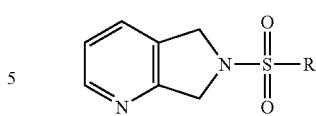

Wherein
R is methyl, ethyl, phenyl, substituted phenyl, tolyl, substituted tolyl, benzyl or substituted benzyl.

(2). reduction of 6-substituted sulfonyl-6,7-dihydro-5H-pyrrolo[3,4-b]pyridine of formula X via catalytic hydrogenation on pyridine ring to form 6-substituted sulfonyl-octahydro-pyrrolo[3,4-b]pyridine of formula XI:

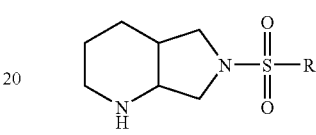

Wherein
R is defined as in step (1).

(3). resolution of formula XI via reacting with enantiomerically pure organic acid, e.g. carboxylic acid or sulphonic acid followed by basifying to convert into free amines of formula XII-a and XII-b.

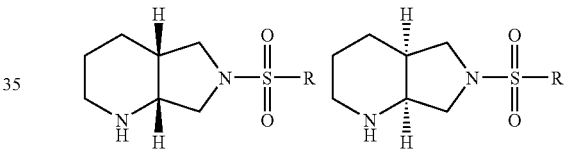

Wherein
R is defined as in step (1).

(4). cleavage of N—S bond of formula XII-a or XII-b by hydrobromic acid/propionic acid/phenol to give free base of formula I-a or I-b respectively after basification.

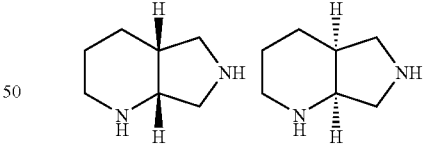

DETAILED DESCRIPTION OF THE INVENTION

Sulfonamide can be considered as a masked NH3 molecule and therefore can be used as the nitrogen source in which electron-withdrawing sulfonyl group enhances the acidity of germinal hydrogens.

Alkylation of sulfonamide under basic condition followed by cleaving N—S bond is one of the simplest preparative methods for pure symmetrical second amines. The utilization of bis-functional alkylating reagents will ultimately result in the formation of cyclic amines.

One appealing property of the resulted sulfonamide is more crystallizable than of the corresponding amides or carbamates. Therefore, the sulfonamide intermediates are easy to be crystallized and separated.

Bearing the advantage of the chemical and physical properties of the sulfonamides in mind the inventors design and execute this novel and economical method, wherein each intermediate is smoothly prepared, separated and identified.

To pursue a practical method for producing the large quantity of the intermediate of compound X to support ongoing reactions a method having practical value must be sought. It is interestingly found that in the first step of the process widely-used chemical sodium ethoxide can be adopted to replace NaH, and DMF can be displaced by the most economical and safe solvent ethanol.

Accordingly, the substituted sulfonamide monosodium salt is conveniently prepared via reaction of sodium ethoxide with appropriate sulfonamide in ethanol solution at elevated temperature for one hour.

The insoluble sulfanilamide monosodium salt is then collected by filtration and dried in vacuum (yield: ~90%). The crude material can be directly used for the coupling reaction without any purification. Optionally, it can be stored in dry ambient condition for months, which is advantageous for manufacturing practice.

Coupling of 2,3-dichloromethylpyridine of formula (VI) with substituted sulfonamide monosodium salt smoothly produces large quantity of 6-substituted sulfonyl-6,7-dihydro-5H-pyrrolo[3,4,b]pyridine of formula X with satisfied yield.

The reduction of the pyridine ring of 6-substituted sulfonyl-6,7-dihydro-5H-pyrrolo[3,4-b]pyridine of formula X is achieved via catalytic hydrogenation. Although $PtO_2$-catalytic hydrogenation running in ethanol at ambient temperature under low pressure (~5 $kg/cm^2$) gives satisfied result, Pd/C-catalytic hydrogenation in acetic acid around 50° C. under 40-60 $kg/cm^2$ pressure gives pure product with high yield (yield >88%) after purification.

The illustration of following steps can be simplified by using the preparation of (S,S)-2,8-diazabicyclo[4.3.0]nonane of formula XII-a as an example. If, instead of preparing its (R,R)-enantiomer, then the methods can be applied according to the illustrated analogously.

The desired S,S-enantiomer is successfully separated out by means of crystallization of the diastereomeric salt from the solution of cis-(S,S/R,R)-6-substituted sulfonyl-6,7-dihydro-5H-pyrrolo[3,4-b]pyridine of formula XI.

Extensive experiments are conducted to search suitable reagents, solvents as well as other resolution facts. The preferable conditions of the separations consist of followings:

The resolution can be carried on by using enantiomerically pure organic acids, e.g. carboxylic acid or sulphonic acids such as mandelic acid, O,O-dibenzoyl-tartaric acid, tartaric acid, malic acid, menthoxyacetic acid, α-methoxy-phenylacetic acid, N-acetyl-L-glutamic acid, N-benzoyl-L-alanine, camphor-3-carboxylic acid, cis-camphoric acid and camphonic-10-sulphonic acid.

The preferable reagents are (S)-(+)-mandelic acid and (D)-(+)-O,O-dibenzoyltartaric acid.

The molar ratio of cis-(S,S/R,R)-6-substituted sulfonyl-6, 7-dihydro-5H-pyrrolo[3,4-b]pyridine of formula XI to (S)-(+)-madelic acid is in range of 1.0:0.5-2.0, preferably from 1.0:1.0-1.2. If (D)-(+)-O,O-dibenzoyltartaric acid is used for the resolution the ratio is in range of 1.0:0.5-1.2.

The resoluting solvent used may select from alcohols, acetone, water, acetonitrile, THF or a solvent mixture consisting from the solvents listed thereof.

Alcohol or water/alcohol mixture is the preferable solvent. The alcohol is preferably selected from methanol, ethanol, 1-propanol, 2-propanol, 1-butanol and 2-butanol. Particularly preference is given to ethanol, methanol, 80-95% ethanol and 80-95% methanol.

The ratio of the volume of alcohol or water/alcohol mixture to the weight of (S)-(+)-madelic acid or (D)-(+)-O,O-dibenzoyltartaric acid is in range of 100:1, preferably in range of 20-30:1.

In the process of the forming the salts the temperatures are, depending on the choice of the alcohol or alcohol/water solvent mixture, in the range of 20° C.-100° C., preferable from 50-80° C.

The temperature for filtration to collect the separated enantiomeric crystals is in the range of 0° C.-20° C.

During the recrystallization process seeding is preferable manner for forming desired enantionmer with high optical purity and chemical yield, but is not absolutely necessary.

The resolution process has the advantages of producing high yield and high enantiomeric excess purity of the desired (S,S)-enantiomer and using economic and environmental-friendly solvents, e.g. ethanol. Furthermore, (S)-(+)-mandelic acid and (D)-(+)-O,O-dibenzoyltartaric acid are both soluble in most of organic solvents, therefore, can be recovered and for reusing.

(R)-(−)-mandelic acid is sold at commercial market for the same price as that of (S)-(+)-mandelic acid. Therefore, (R)-(−)-mandelic acid is also tested for the resolution under similar condition. As expected, (R,R)-6-substituted sulfonyl-6,7-dihydro-5H-pyrrolo[3,4-b]pyridine of formula XII-b is first separated out with high yield and optical purity. As such, it leave the possibility that the (S,S)-enantiomer may also be obtained from the mother liquid, wherein only small portion of (R,R)-6-substituted sulfonyl-6,7-dihydro-5H-pyrrolo[3,4-b]pyridine left, which may be removed by simple recrystallization.

The enantiomerically pure title product of formula I-a is obtained after breaking N—S bond existing in formula XII-a. Several methods are examined. A modified method reported in *J. Am. Chem. Soc;* 75. 3630 (1953) by D. I. Weisblat et al gives the better result, wherein the intermediate is heated with a mixed solution of 48% hydrobromic acid, propionic acid and phenol under reflux for 5-7 hours.

The N—S bond existing in the sulfonamides may also be cleaved by the conventional methods cited in *"Protective group in organic synthesis"*, 377-386 (1991) by T. Greene and P. M. Wuts, John Wiley & Sons, N.Y.

Optionally, for the commercial purpose of storage and transportation the free base of formula I-a is converted into its stable di-hydrobromic acid salt, The following examples further illustrate the specific aspects of the present process and are not intended to limit the scope thereof in any respect and should not be so construed.

Example 1

The Preparation of 2,3-dichloromethylpyridine (Formula VI)

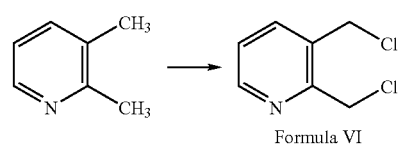

Formula VI 2,3-Dichloromethylpyridine is prepared following a modified method of L. H. Klemm et al; *J. Heterocyclic Chem.* 7. 463 (1970) and U.S. Pat. No. 3,709,894.

Example 2

The Preparation of 6-(toluene-4-sulfonyl)-6,7-dihydro-5H-pyrrolo[3,4-b]pyridine (formula XI-a):

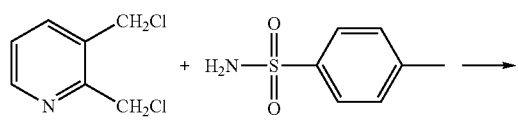

Formula VI

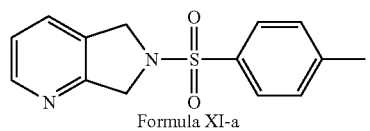

Formula XI-a

To a stirred solution of sodium ethoxide (23.8 g) in ethanol (anhydrous, 400 ml) is added toluene-4-sulfonamide (60 g) around 50 C. The formed slurry is heated up to reflux for 2 hours and then cooled to 20° C. The precipitated solid is collected by filtration, rinsed with anhydrous ethanol and dried under vacuum with nitrogen flow to give toluene-4-sulfonamide monosodium salt (61.3 g, yield: 90.6%).

DMF (600 ml) is added to toluene-4-sulfonamide monosodium salt (20 g) under nitrogen. The mixture is heated to 70-75° C., to which 2,3-dichloromethylpyridine (18.2 g) in DMF (120 ml) is added in 30 minutes. After stirred for 1 hour at same temperature an additional toluene-4-sulfonamide monosodium salt (20 g) is added. The mixture is continuously heated 1 hour at 75-80° C. DMF is then removed by vacuum evaporation. To the residue is added aqueous sodium hydroxide solution (1 N, 150 ml) followed by extraction with chloroform (200 ml). The separated aqueous phase is re-extracted with chloroform (200 ml×3). The combined extracts are washed with water (50 ml) and subjected to azeotropic evaporating to remove the residual water. The crude 6-(toluene-4-sulfonyl)-6,7-dihydro-5H-pyrrolo[3,4-b]pyridine (formula XI-a) is subjected to recrystallization from ethanol (400 ml) to afford 22.8 g of title product as white solid (yield 80.5%).

Melting point: 194-196 C (dec); $^1$H-NMR (CDCl$_3$, δ): 2.40 (3H, s), 4.63 (4H, d), 7.18 (1H, m), 7.35 (2H, d), 7.53 (1H, d), 7.78 (2H, d), 8.43 (1H, d);

Example 3

The Preparation of 6-benzenesulfonyl-6,7-dihydro-5H-pyrrolo[3,4-b]pyridine (formula XI-b)

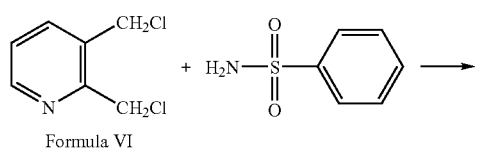

Formula VI

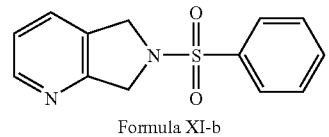

Formula XI-b 2,3-Chlorodimethylpyridine (4.0 g) and benzenesulfonamide mono-sodium salt (4.1 g+4.1 g) are treated in DMF (200 ml+45 ml) according to the same method as that of example 2 to give the title compound (4.7 g) as white solid after de-colorization with activated carbon and recrystallization from ethanol (60 ml) (yield: 79.0%).

Melting point: 160-162 C; LC-MS: 261.04; $^1$H-NMR (CDCl$_3$, δ) 2.92 (3H, s), 4.74 (4H, dd), 7.25 (1H, dd), 7.60 (1H, d), 8.52 (1H, d).

Example 4

The Preparation of 6-methanesulfonyl-6,7-dihydro-5H-pyrrolo[3,4-b]pyridine (formula XI-c)

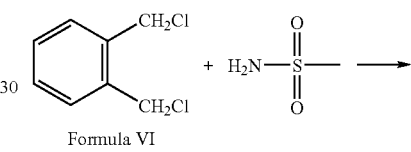

Formula VI

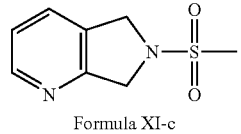

Formula XI-c 2,3-Chlorodimethylpyridine (4.0 g) and methanesulfonamide mono-sodium salt (2.66 g+2.66 g) are treated in DMF (140 ml+45 ml) according to the same method as that of example 2 to give the title compound as white solid (2.5 g) after de-colorization with activated carbon and recrystallization from ethanol (50 ml) (yield: 55.6%).

Melting point: 150-152° C.; LC-MS: 199.09; $^1$H-NMR (CDCl$_3$, δ) 4.66 (4H, dd), 7.15 (1H, dd), 7.55 (4H, m), 7.90 (2H, dd), 8.43 (1H, d)

Example 5

The Preparation of 6-(toluene-4-sulfonyl)-octahydro-pyrrolo[3,4-b]pyridine (formula XII)

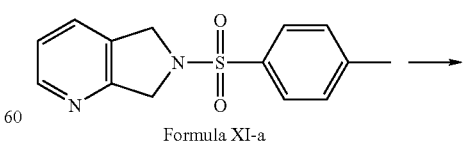

Formula XI-a

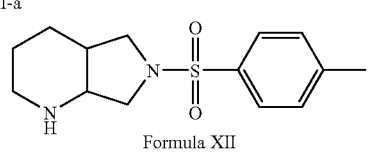

Formula XII

Palladium on carbon (10%) (20.0 g) is placed into reactor under nitrogen flow followed by adding the solution of 6-(toluene-4-sulfonyl)-6,7-dihydro-5H-pyrrolo[3,4-b]pyridine (formula XI-a) (60.8 g) is acetic acid (600 ml). Hydrogen is introduced till pressure reaches to 60 kg/cm².

The hydrogenation is run around 50° C. under same pressure for 5 hours. After cooling down to 20-30° C. hydrogen is released and replaced by nitrogen. The reaction mixture is filtered and concentrated. To the residue sodium hydroxide aqueous solution (30%) (150 ml) is added to adjust pH>11-12. The solution is extracted with chloroform (350 ml×3). The extracted solutions are washed with water and evaporated under reduced pressure to give an oily residue, to which MTBE is added and stirred for 30 minutes. The precipitated product is collected, dried in vacuum oven to give 55.4 g of solid. (yield=89.2%)

Melting point: 95-97° C.; LC-MS: 281.16; ¹H-NMR (CDCl₃, δ): 1.37 (2H, m), 1.40 (2H, m), 2.04 (1H, m), 2.43 (3H, s), 2.51 (1H, m), 2.82 (1H, m), 3.22 (2H, m), 331 (3H, m), 7.30 (2H, d), 7.73 (2H, d).

Example 6

The preparation of (S,S)-6-(toluene-4-sulfonyl)-octahydro-pyrrolo[3,4-b]pyridine (formula XII-a) (Method 1)

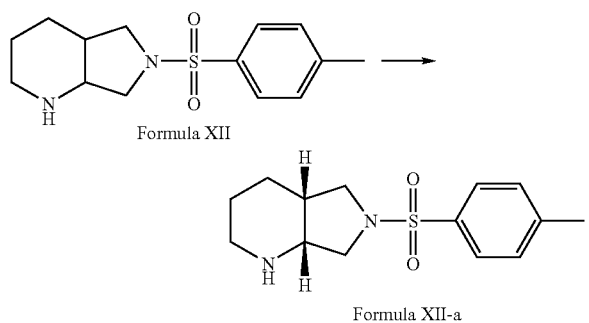

6-(Toluene-4-sulfonyl)-octahydro-pyrrolo[3,4-b]pyridine (30.0 g) dissolves in anhydrous ethanol (270 ml) at 70-75° C., to which is added a solution of (S)-(+)-mandelic acid (16.8 g) in anhydrous ethanol (150 ml). The solution is heated to reflux for 45 minutes and then cooled slowly to 20° C. After maintaining at same temperature for 1 hour the precipitated crystals are collected by filtration, dried to give 21.9 g of white solid.

21.9 g of the crude product is mixed with anhydrous ethanol (350 ml) and heated to reflux for 30 minutes. After cooling down to 40-45 C seeding is conducted. The slightly cloudy solution is slowly cooled down to 15-20° C. and continued to stir for 3 hours. The white crystals are collected, dried in vacuum oven under nitrogen flow to give 19.1 g of the salt as white crystal. (Theoretical yield: 81.6%)

Melting point: 170-173° C.; [α]$_D$=+30.08° (H₂O, C=1).

¹H-NMR (CD₃OD, δ) 1.67 (4H, br), 2.24 (1H, m), 2.44 (3H, s), 2.87 (1H, m), 3.14 (1H, dd), 3.29 (3H, m), 3.34 (1H, m), 3.49 (1H, dt), 3.58 (1H, m), 7.22 (1H, t), 7.29 (2H, t), 7.45 (4H, dd), 7.74 (2H, d).

Liberation of the base:

(S)-(+)-mandelic acid salt (15.0 g) is mixed with water (55 ml), to which sodium hydroxide (25%) is dropped in till pH=11-12 and extracted with chloroform (50 ml×4). The combined organic phases are washed with water (35 ml) and then subjected to azeotropic distillation to remove the residual water to afford (S,S)-6-(toluene-4-sulfonyl)-octahydro-pyrrolo[3,4-b]pyridine base (9.7 g) as white crystal. (yield: 100%)

Melting point: 102-104° C.; [α]$_D$=+2.32° (ethanol, C=1); ee>99% (determined by ¹H-NMR (CDCl₃, δ) after derivatization with Mosher's acid chloride)

LC-MS: 281.06; ¹H-NMR (CDCl₃, δ): 1.37 (2H, m), 1.40 (2H, m), 2.04 (1H, m), 2.43 (3H, s), 2.51 (1H, m), 2.82 (1H, m), 3.22 (2H, m), 3.31 (3H, m), 7.30 (2H, d), 7.73 (2H, d)

Example 7

The preparation of (R,R)-6-(toluene-4-sulfonyl)-octahydro-pyrrolo[3,4-b]pyridine (formula XII-b) (Method 1)

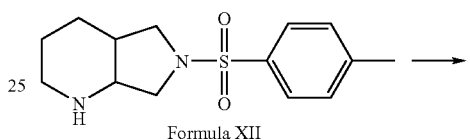

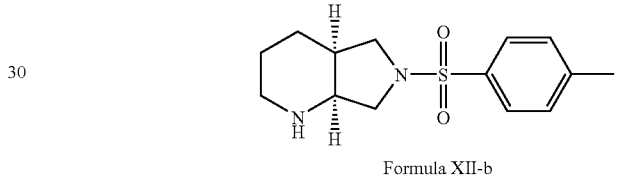

6-(Toluene-4-sulfonyl)-octahydro-pyrrolo[3,4-b]pyridine (50.0 g) dissolves in anhydrous ethanol (550 ml) at 70° C.-75° C., to which is added a solution of (R)-(-)-mandelic acid (28.6 g) in anhydrous ethanol (215 ml). The solution is heated to reflux for 30 minutes and then cooled slowly to 20° C. After maintaining at same temperature for 2 hours the precipitated crystals are collected by filtration, rinsed with anhydrous ethanol, dried to give 36.2 g of white solid.

36.2 g of crude product is mixed with anhydrous ethanol (610 ml) and heated to reflux for 30 minutes, then slowly cooled down to 20° C. and continued to stir for 2 hours. The white crystals are collected, dried in vacuum oven under nitrogen flow to give 30.6 g of the salt as white crystal (Theoretical yield: 77.8%).

Melting point: 169-173° C.; [α]$_D$=-29.96° (H₂O, C=1).

¹H-NMR (CD₃OD, δ) 1.67 (4H, br), 2.24 (1H, m), 2.44 (3H, s), 2.87 (1H, m), 3.14 (1H, dd), 3.29 (3H, m), 3.34 (1H, m), 3.49 (1H, dt), 3.58 (1H, m), 7.22 (1H, t), 7.29 (2H, t), 7.45 (4H, dd), 7.74 (2H, d)

Liberation of the base:

The (R)-(-)-mandelic acid salt (30.0 g) is mixed with water (100 ml), to which sodium hydroxide (25%) is added till pH=12 and extracted with chloroform (300 ml×4). After the same work up procedure described in example (R,R)-6-(toluene-4-sulfonyl)-octahydro-pyrrolo[3,4-b]pyridine (19.2 g) is obtained as white crystal (yield: 98.9%)

Melting point: 103-104° C.; [α]$_D$=-2.66° (ethanol, C=1); ee>99% (determined by 1H-NMR (CDCl₃, δ) after derivatization with Mosher's acid chloride)

LC-MS: 281.06; ¹H-NMR (CDCl₃): 1.37 (2H, m), 1.40 (2H, m), 2.04 (1H, m), 2.43 (3H, s), 2.51 (1H, m), 2.82 (1H, m), 3.22 (2H, m), 33.1 (3H, m), 7.30 (2H, d), 7.73 (2H, d)

Example 8

The preparation of (S,S)-6-(toluene-4-sulfonyl)-octahydro-pyrrolo[3,4-b]pyridine (Formula XII-a) (Method 2)

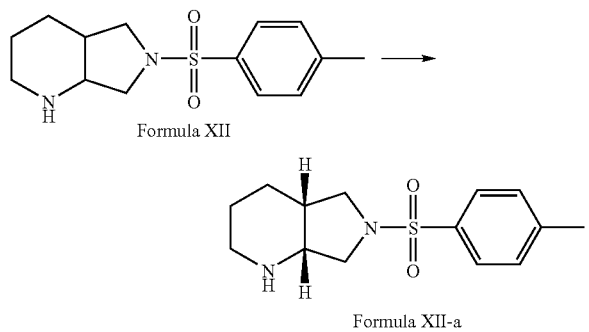

6-(Toluene-4-sulfonyl)-octahydro-pyrrolo[3,4-b]pyridine (5.0 g) dissolves in anhydrous ethanol (47.5 ml) at 70° C.-75° C., to which is added a solution of (D)-(+)-O,O-dibenzoyltartaric acid (3.5 g) in anhydrous ethanol (30 ml). The solution is heated to reflux for 60 minutes and then cooled slowly to 20° C. After maintaining at same temperature for 2.5 hour the precipitated crystals are collected by filtration and rinsed with ethanol and directly used for purification.

The wet crude product is mixed with anhydrous ethanol (50 ml) and heated to reflux for 30 minutes, then slowly cooled down to 20° C. and continued to stir for 3 hours. The solid is collected, dried in vacuum oven under nitrogen flow to give 3.3 g of purified (S,S)-6-(toluene-4-sulfonyl)-octahydro-pyrrolo[3,4-b]pyridine. ½ (D)-(+)-O,O-dibenzoyltartaric acid salt as white solid (Theoretical yield: 77.6%)

Melting point: 170-172° C. (contracts at 82° C.); $[\alpha]_D$=+46.43° (H₂O, C=1)

LC-MS: 281.10 and 380.99; ¹H-NMR (CD₃OD, δ): 1.62 (4H, br), 2.20 (1H, br), 2.43 (3H, s), 2.87 (1H, br) 3.12 (1H, d), 3.29 (3H, m), 3.51 (1H, d) 3.60 (1H, d), 7.42 (4H, dd), 7.58 (1H, t), 7.72 (2H, d), 8.16 (2H, d), Liberation of the base:

(S,S)-6-(toluene-4-sulfonyl)-octahydro-pyrrolo[3,4-b]pyridine. ½ (D)-(+)-O,O-dibenzoyl tartaric acid salt (2.7 g) is dissolved in chloroform (100 ml), to which water (30 ml) is added, basified by sodium hydroxide (25%) till pH=11-12. The separated aqueous phase is extracted with chloroform (150 ml×2). The combined organic phases are washed with water (25 ml) and dried over Na2SO4. After evaporating the residue is stirred with MTBE for 30 minutes. The solid is collected by filtration, dried in vacuum to give the title compound (1.49 g) as white crystals (yield: 90.8%).

$[\alpha]_D$=+2.65° (ethanol, C=1); ee>98.5%, (determined by ¹H-NMR (CDCl₃, δ) after derivatization with Mosher's acid chloride)

Example 9

The preparation of (R,R)-6-(toluene-4-sulfonyl)-octahydro-pyrrolo[3,4-b]pyridine (Formula XII-b) (Method 2)

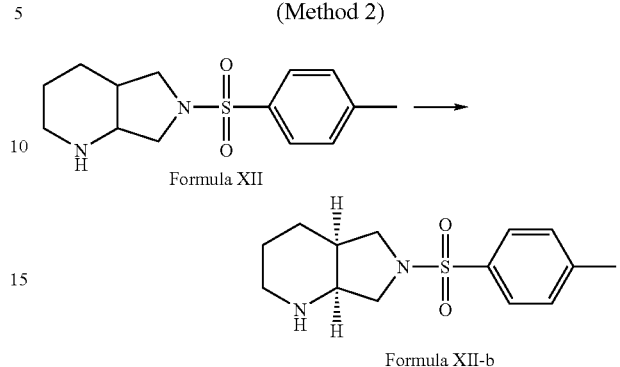

6-(Toluene-4-sulfonyl)-octahydro-pyrrolo[3,4-b]pyridine (5.0 g) dissolves in anhydrous ethanol (47.5 ml) at 70° C.-75° C., to which is added a solution of (L)-(−)-O,O-dibenzoyltartaric acid (3.5 g) in anhydrous ethanol (30.0 ml). The solution is heated to reflux for 60 minutes and then cooled slowly to 20° C. After maintaining at same temperature for 2.5 hour the precipitated solid is collected by filtration and used directly for purification.

The wet crude product is mixed with anhydrous ethanol (70 ml) and heated to reflux for 30 minutes, then slowly cooled down to 20° C. and continued to stir for 3 hours. The white crystals are collected, dried in vacuum oven under nitrogen flow to give 3.80 g of the purified (S,S)-6-(toluene-4-sulfonyl)-octahydro-pyrrolo[3,4-b]pyridine. ½ (D)-(+)-O,O-dibenzoyltartaric acid salt (Theoretical yield: 89.4%).

Melting point: 171-173° C. (contracts at 75° C.); $[\alpha]_D$=−39.56° (ethanol, C=1);

LC-MS: 281.10 and 380.99; ¹H-NMR (CD₃OD, δ): 1.62 (5H, br), 2.20 (1H, br), 2.43 (3H, s), 2.87 (1H, br) 3.12 (1H, d), 3.29 (3H, m), 3.51 (1H, d) 3.60 (1H, d), 7.42 (4H, dd), 7.58 (1H, t), 7.72 (2H, d), 8.16 (2H, d).

Liberation of the base:

(R,R)-6-(toluene-4-sulfonyl)-octahydro-pyrrolo[3,4-b] pyridine ½ (L)-(−)-O,O-dibenzoyl tartaric acid salt (3.0 g) is dissolved in water (50 ml). The solution is basified by sodium hydroxide (30%) till pH=11-12 and extracted with chloroform (80 ml×3). After same work up procedure as described in example 7 the oil obtained is turned to white solid (1.80 g) after slurry with MTBE and drying in vacuum (yield 100%).

$[\alpha]_D$=−2.31° (ethanol, C=1); ee>98.5%, (determined by ¹H-NMR (CDCl₃, δ) after derivatization with Mosher's acid chloride)

Example 10

The preparation of (S,S)-2,8-diazabicyclo[4.3.0]nonane (Formula I-a)

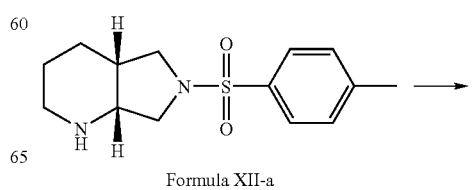

-continued

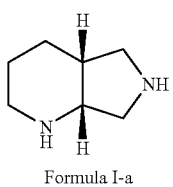

Formula I-a (S,S)-6-(toluene-4-sulfonyl)-octahydro-pyrrolo[3,4-b]pyridine (20.1 g) is dissolved in hydrobromic acid (48%, 130 ml). To the solution are added propionic acid (60 ml) and phenol (12.2 g) The mixture is heated to reflux for 6-7 hours. After completing the reaction the mixture is cooled to ambient temperature and concentrated to dryness.

The residue is dissolved in water (100 ml), extracted with MTBE (100 ml) and re-extracted with ethyl acetate (100 ml). The aqueous solution is separated out, adjusted to pH=11-12 by sodium hydroxide (40%), saturated with sodium chloride, then extracted by chloroform (250 ml×4). After conventional work up and distillation 7.3 g of oil is obtained (yield: 80.1%).

GC: 99.8%; $[\alpha]_D$=−2.50° (H$_2$O, C=1); ee>99% (determined by gas chromatography after derivatisation with Mosher's reagent).

$^1$H-NMR (CDCl$_{3, \delta}$): 1.40 (1H, m), 1.51 (1H, m), 1.62 (2H, m), 2.21 (2H, br), 2.49 (1H, m), 2.57 (1H, td), 2.74 (1H, d), 2.93 (4H, m), 3.13 (1H, t).

The free base is converted to di-hydrobromic acid salt in a solvent mixture of hydrobromic acid/ethanol. Melting point: 300-304° C.; $[\alpha]_D$=+4.22° (H$_2$O, C=1).

Example 11

The preparation of (R,R)-2,8-diazabicyclo[4.3.0]nonane (Formula I-b)

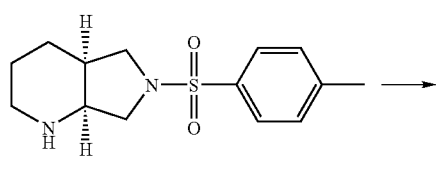

Formula XII-b

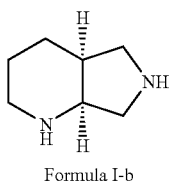

Formula I-b

The title compound (9.12 g) is prepared from mixture system of (R,R)-6-(toluene-4-sulfonyl)-octahydro-pyrrolo [3,4-b]pyridine (24.0 g), hydrobromic acid (48%, 156 ml), propionic acid (72 ml) and phenol (14.6 g) following the same procedure described in example 9. After conventional work up and distillation 3.4 g of oil is obtained (yield: 78.0%).

$[\alpha]_D$=+2.33° (H$_2$O, C=1); ee>99% (determined by gas chromatography after derivatisation with Mosher's reagent).

$^1$H-NMR (CDCl$_3$): 1.40 (1H, m), 1.51 (1H, m), 1.62 (2H, m), 2.21 (2H, br), 2.49 (1H, m), 2.57 (1H, td), 2.74 (1H, d), 2.93 (4H, m), 3.13 (1H, t).

The free base is converted to di-hydrobromic acid salt in a solvent mixture of hydrobromic acid/ethanol. Melting point: 301-305° C.; $[\alpha]_D$=−4.38° (H$_2$O, C=1).

What is claimed is:

1. A method for producing (S,S)-2,8-diazabicyclo[4.3.0] nonane of formula I-a and its enantiomer (R,R)-2,8-diazabicyclo[4.3.0]nonane of formula I-b

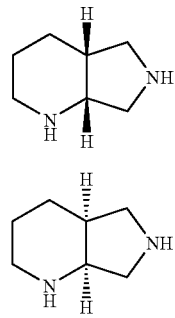

formula I-a formula I-b which process comprises:
(a). N-alkylation of formula VI

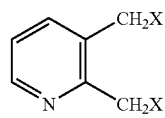

where X is selected from Cl, Br and I at each occurrence, with substituted sulfonamide to form an intermediate of formula X

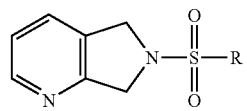

where R is C$_1$-C$_5$alkyl, phenyl, substituted phenyl, tolyl, substituted tolyl, benzyl, or substituted benzyl;

(b). reducing the intermediate of formula X by catalytic hydrogenation to give formula XI

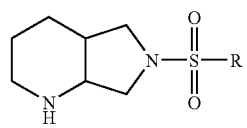

(c). resolution of formula XI with enantiomerically pure carboxylic acid or sulphonic acid followed by basifying to result in formula XII-a and its enanatiomer XII-b formula XII-a

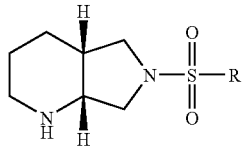

-continued

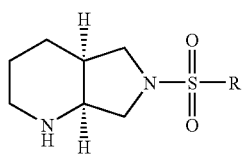

formula XII-b (d). cleaving the N-sulfonyl bond of formula XII-a or formula XII-b to give the title product of formula I-a or I-b

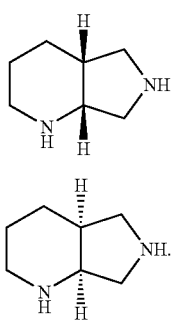

formula I-a formula I-b

2. The method according to claim 1, wherein R is selected from the group consisting of methyl, ethyl, phenyl, substituted phenyl, tolyl, substituted tolyl, benzyl and substituted benzyl.

3. The method according to claim 1, wherein the catalytic hydrogenation of formula X is effected with a catalyst selected from the group consisting of Pd—C, palladium hydroxide, palladium chloride, palladium oxide, palladium, Raney-nickel, $PtO_2$, ruthenium and rhodium.

4. The method according to claim 1, wherein the catalytic hydrogenation of formula X is performed in a solvent selected from the group consisting of acetic acid, ethanol, methanol, ethyl acetate, ethanol containing HCl, methanol containing HCl, ethanol containing HBr, methanol containing HBr, ethyl acetate containing HCl or any solvent mixture of the foregoing solvents.

5. The method according to claim 1, wherein the catalytic hydrogenation of formula X is performed at a temperature of 20° C. to 80° C.

6. The method according to claim 1, wherein the catalytic hydrogenation of formula X is performed under an applied reduction pressure and the reduction pressure is from atmospheric pressure to 100 $kg/cm^2$.

7. The method according to claim 1, wherein the enantiomerically pure carboxylic acid or enantiomerically pure sulphonic acid is selected from the group consisting of mandelic acid, O,O-dibenzoyl-tartaric acid, tartaric acid, malic acid, menthoxyacetic acid, α-methoxy-phenylacetic acid, N-acetyl-L-glutamic acid, N-benzoyl-L-alanine, camphor-3-carboxylic acid, cis-camphoric acid and camphonic-10-sulphonic acid.

8. The method according to claim 1, wherein racemic base of formula XI is present in a molar ratio of racemic base: resolving reagent of from 1.0:0.5 to 1.0:2.0.

9. The method according to claim 1, wherein the resolution of formula XI is performed in a solvent selected from the group consisting of ethanol, methanol, 1-propanol, 2-propanol, acetone, acetonitrile, or in a mixed solvent system selected from the group consisting of ethanol/water, methanol/water, acetone/water, acetonitrile/water, 1-propanol/water, and 2-propanol/water.

10. The method according to claim 9, wherein the acid used for resolution of formula XI is (S)-(+)-mandelic acid or (D)-(+)-O,O-dibenzoyltartaric acid and the solvent used for resolution is present in a volume to weight ratio with the acid used for resolution of 100:1.

11. The method according to claim 1, wherein the N-sulfonyl bond of formula XII-a or formula XII-b is cleaved using a cleaving reagent selected from the group consisting of Raney-nickel, HBr gas/acetic acid, hydrobromic acid/carboxylic acid/phenol, hydroiodic acid, hydrogen fluoride/anisole, $LiAlH_4$, Red-Al, sodium naphthaenide, $HClO_4/AcOH$ and $Na/NH_3$.

12. The method according to claim 9, wherein the acid used for resolution of formula XI is (S)-(+)-mandelic acid or (D)-(+)-O,O-dibenzoyltartaric acid and the solvent used for resolution is present volume to weight ratio with the acid used for resolution of 20:1 to 40:1.

* * * * *